(12) United States Patent
Maa et al.

(10) Patent No.: US 12,048,078 B2
(45) Date of Patent: Jul. 23, 2024

(54) SPECTRAL POWER DISTRIBUTION FUSION LIGHTING APPARATUS

(71) Applicant: Aleddra Inc., Renton, WA (US)

(72) Inventors: Chia-Yiu Maa, Bellevue, WA (US); Li-Jyuan Luo, Taipei (TW); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 168 days.

(21) Appl. No.: 17/981,123

(22) Filed: Nov. 4, 2022

(65) Prior Publication Data

US 2023/0057171 A1 Feb. 23, 2023

Related U.S. Application Data

(63) Continuation-in-part of application No. 17/509,877, filed on Oct. 25, 2021, now abandoned, which is a continuation-in-part of application No. 17/148,277, filed on Jan. 13, 2021, now Pat. No. 11,191,863, which is a continuation-in-part of application No. 17/094,567, filed on Nov. 10, 2020, now Pat. No. 11,103,612, which is a continuation-in-part of application No. 16/180,416, filed on Nov. 5, 2018, now Pat. No. 10,874,762.

(51) Int. Cl.
*H05B 47/155* (2020.01)
*A61M 21/00* (2006.01)
*A61N 5/06* (2006.01)
*G10K 15/02* (2006.01)
*H05B 45/30* (2020.01)

(52) U.S. Cl.
CPC ........... *H05B 47/155* (2020.01); *A61M 21/00* (2013.01); *A61N 5/0618* (2013.01); *G10K 15/02* (2013.01); *H05B 45/30* (2020.01); *A61M 2021/0027* (2013.01); *A61M 2205/051* (2013.01); *A61N 2005/0663* (2013.01)

(58) Field of Classification Search
CPC .... A61N 2005/0663; A61N 2005/0651; A61N 2005/0662; H05B 45/30; H05B 45/20; A61M 2205/051
See application file for complete search history.

(56) References Cited

U.S. PATENT DOCUMENTS

| | | | |
|---|---|---|---|
| 2015/0123564 A1* | 5/2015 | Simonian | H05B 47/135 315/294 |
| 2015/0312975 A1* | 10/2015 | Tischler | H01S 5/042 315/294 |
| 2021/0162912 A1* | 6/2021 | Spero | H05B 45/395 |

* cited by examiner

*Primary Examiner* — Monica C King
(74) *Attorney, Agent, or Firm* — Han IP PLLC; Andy M. Han (57) ABSTRACT

A spectral power distribution (SPD) fusion lighting apparatus includes a first visible light source with a first SPD, a second visible light source with a second SPD, a driver circuit, and a controller. The first SPD is different than the second SPD markedly in a 50 nm wavelength range. The controller toggles the turning on of the first visible light and the second visible light at a frequency greater than 25 Hz. The first visible light source is turned on during one half of the duty cycle, whereas the second visible light source is turned on during the other half of the duty cycle. The first visible light source and the second visible light emit similar light outputs and have similar chromaticity coordinates on the CIE 1931 color space chromaticity diagram. In some embodiments a sound wave generator is used to generate a sound wave at the same frequency.

16 Claims, 6 Drawing Sheets

SPECTRAL POWER DISTRIBUTION FUSION LIGHTING APPARATUS

CROSS REFERENCE TO RELATED PATENT APPLICATIONS

The present disclosure is a continuation-in-part (CIP) of U.S. patent application Ser. No. 17/509,877, filed 25 Oct. 2021 as a CIP of U.S. patent application Ser. No. 17/148,277, filed 13 Jan. 2021 and issued as U.S. Pat. No. 11,191,863 on 7 Dec. 2021, which is a CIP of U.S. patent application Ser. No. 17/094,567, filed 10 Nov. 2020 and issued as U.S. Pat. No. 11,103,612 on 31 Aug. 2021, which is a CIP of U.S. patent application Ser. No. 16/180,416, filed 5 Nov. 2018 and issued as U.S. Pat. No. 10,874,762 on 29 Dec. 2020. Contents of aforementioned applications are herein incorporated by reference in their entirety.

BACKGROUND

Technical Field

The present disclosure pertains to the field of lighting apparatuses and, more specifically, proposes a spectral power distribution (SPD) fusion lighting apparatus.

Description of Related Art

It has been discovered that by flickering a light at a frequency between 35 to 45 Hz or generating a sound at a similar frequency has the effect of stimulating the cells in certain region of the brain, resulting in using a flicking light or a sound at such a frequency for treating Alzheimer's disease. In U.S. patent application Ser. No. 17/509,877, a multi-mode lighting device was introduced. The controlling mechanism of that lighting device is configured to either flash the light output of the visible light source at a frequency in a frequency range of 35~45 Hz or generate an audible sound at a frequency in a frequency range of 35~45 Hz, or both. However, flicking a light source on and off at 35 to 45 Hz is uncomfortable for human eyes. Some patients may be resistant to such uncomfortable treatment, thus rendering the treatment ineffective.

It is known that when strobing two light sources each with a different color at a frequency greater than 25 Hz, human eyes cannot distinguish the individual colors. Human visual system would blend the two colors into a third color. If the colors of the two light sources are sufficiently similar but each has a different SPD, then the two light sources would appear to be the same to human eyes at 35 to 45 Hz yet their different SPD's could still be picked up by the non-visual photoreceptor of the eyes, namely intrinsically photosensitive retinal ganglion cells (ipRGCs), resulting in a stimulation of the brain cells just like the turning on/off of a light source at 35 to 45 Hz yet without the discomfort to the eyes.

The present disclosure proposes a lighting apparatus that toggles two light sources with similar chromaticity coordinates but different SPDs at a frequency between 35 to 45 Hz, such that human eyes would not pick up the visual difference of the lights emitted from the two light sources, but the ipRGCs still detect the difference between the two SPD's, leading to a sufficient stimulation of certain brain cells.

SUMMARY

In one aspect, the SPD fusion lighting apparatus comprises a first visible light source with a first SPD, a second visible light source with a second SPD, a driver circuit, and a controller. The first SPD is different from the second SPD in that in a 50 nm wavelength range within [380 nm, 750 nm] the percentage of the first SPD in this 50 nm wavelength range differs more than 5% over the percentage of the second SPD in this 50 nm wavelength range. For example, the percentage of the first SPD in [465 nm, 515 nm] range is 14%, whereas the percentage of the second SPD in this wavelength range is merely 5%. The chromaticity (x, y) coordinate of the light emitted by the first visible light source on the International Commission on Illumination in 1931 (CIE 1931) color space chromaticity diagram is adjacent to the chromaticity (x, y) coordinate of the light emitted by the second visible light source on the CIE 1931 color space chromaticity diagram. The chromaticity coordinate of the light emitted by the first visible light source is not required to be the same as the chromaticity coordinate of the light emitted by the second visible light source. It is only necessary that they are close enough to each other to the extend they are not distinguishable by human eyes. The controller is configured to toggle the turning on of the first visible light source and the second visible light source at a toggling frequency>25 Hz. The first visible light source is turned on during one half of the duty cycle (though not necessarily to be on for the entire half cycle), whereas the second visible light source is turned on during the other half of the duty cycle (though not necessarily to be on for the entire other half cycle). The first visible light source and the second visible light source emit similar light outputs (lumens). The driver circuit converts an external power to a fixed internal power to power either the first visible light source or the second visible light source (but never both simultaneously) according to the controller's toggling operation between the first visible light source and the second visible light source.

For the SPD fusion to work properly, the first visible light source and the second visible light source must be similar enough human eye's visual system and at the same time different enough to human eye's non-visual system. Similar enough so that the eyes are not able to distinguish them visually, but different enough so that ipRGCs can still tell them apart. To ensure they are different enough, it is required that their SPD's differ markedly in one 50 nm wavelength range by 5%. For example, the first visible light source may have 14% SPD in the [465 nm, 515 nm] wavelength range, and the second visible light source may have merely 5% SPD in the same wavelength range. The reason for choosing more than 5% SPD difference between the first and the second light sources is empirical. Human visual system is an analog system. If the color of two light sources differs less than 5%, most people cannot tell them apart. It is thus reasonable to assume ipRGCs have similar sensitivity level and will not tell apart two light sources if their color difference or their SPD difference is less than 5%. Therefore, more than 5% SPD difference is set between the first visible light source and the second visible light source in one 50 nm wavelength. It is foreseeable to choose a higher SPD difference in practice, for example, 9% or 10% or even higher, to provide a stronger simulation to ipRGCs.

Figure 1:
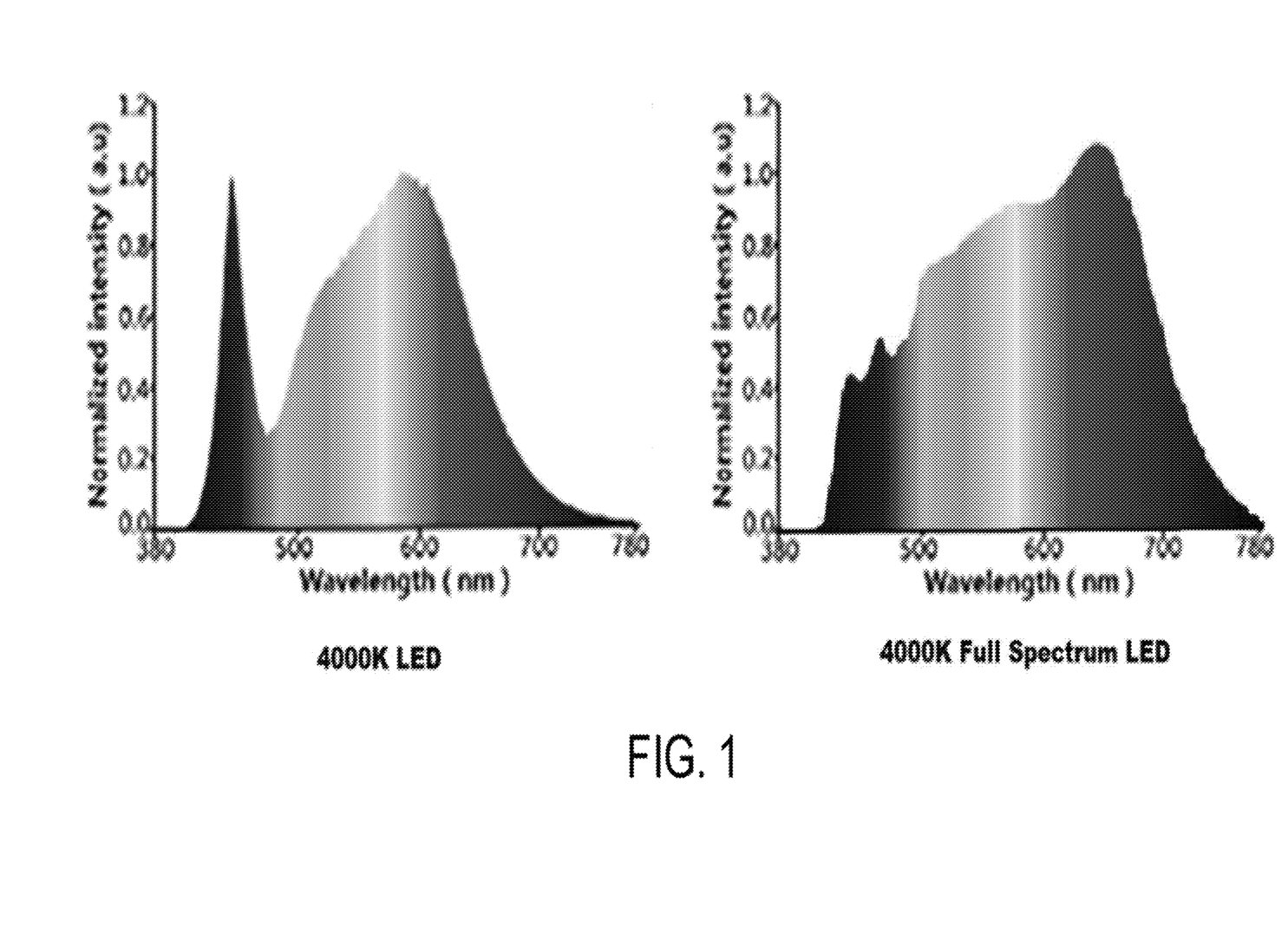
FIG. 1 schematically depicts the SPD of an incandescent light source and the SPD of a warm LED light source emulating the color temperature of the incandescent light source.
Figure 2:
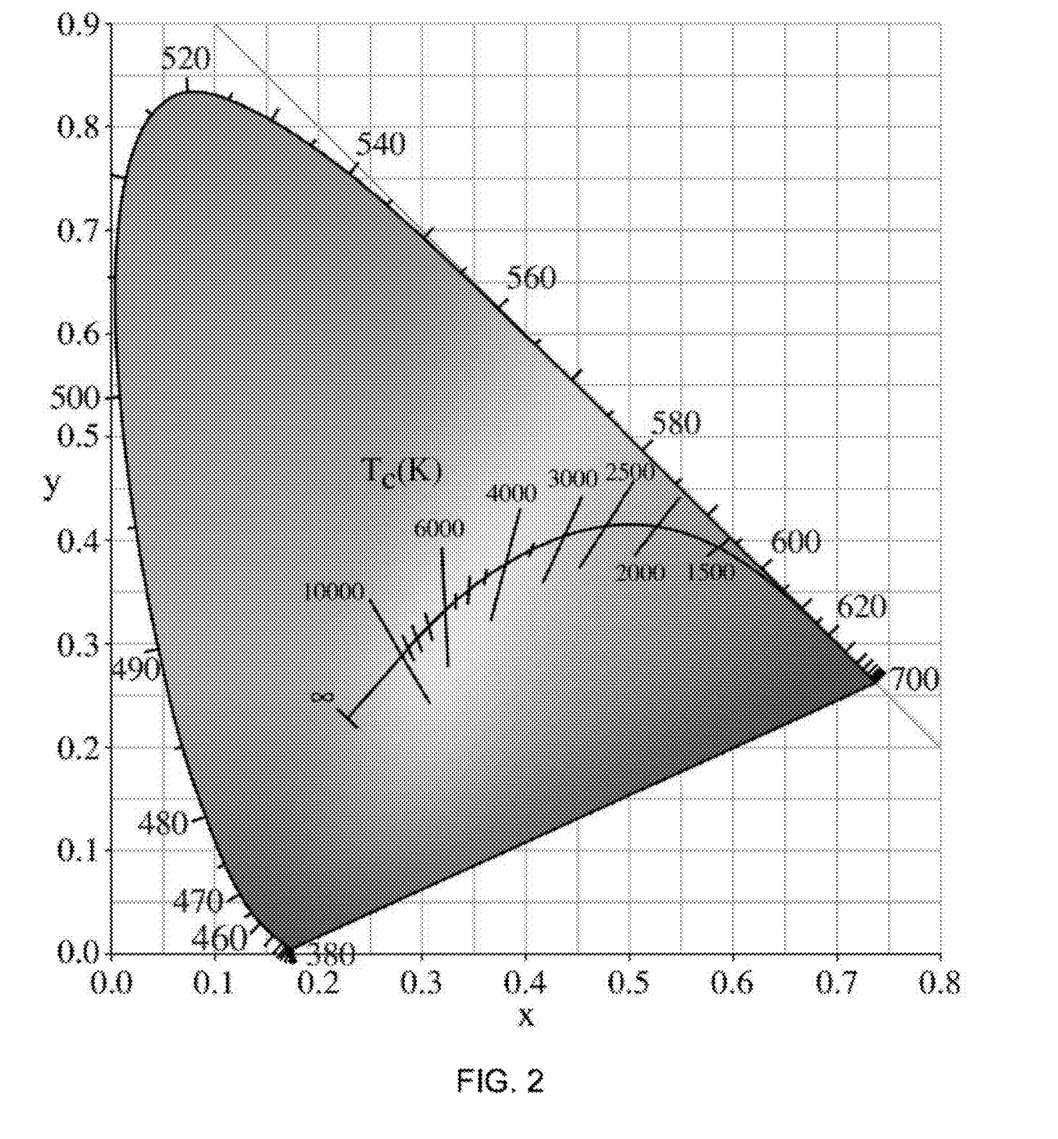
FIG. 2 shows the CIE 1931 color space chromaticity diagram with color temperature lines.

FIG. 1 shows the SPD of a typical 4000K LED light source and the SPD of 4000K full spectrum LED light source. They have the same color temperature 4000K and the same chromaticity coordinate on the CIE 1931 color space chromaticity diagram (FIG. 2). Their SPDs differ more than 5% in the [465 nm, 515 nm]. When toggling these two light sources at a similar light output level at a toggling frequency>25 Hz, human eyes will not be able to tell them apart.

To ensure the first visible light source and the second visible light source are similar enough to human eyes, it is necessary that they have similar light outputs. If their light outputs differ markedly, then human eyes could perceive strobing, which defeats the SPD fusion purpose of two light sources. Moreover, to ensure the first visible light source and the second visible light source are similar enough, it is also critical that they have similar the chromaticity (x, y) coordinates on the CIE 1931 color space chromaticity diagram. With this condition, the eyes would regard the light emitted by the first light sources and the light emitted by the second visible light source to be the same, visually speaking. Some may be argued that it is sufficient to require the first visible light source and the second visible light source have a same color temperature. However, it can be seen from the CIE 1931 color space chromaticity diagram in FIG. 2, there are more than one chromaticity coordinates to achieve the same color temperatures and they could still be visually distinguishable. For example, considering the two chromaticity coordinates on the opposite end of the 4000K color temperature line, one chromaticity coordinate is more yellow-green whereas the other chromaticity coordinate is more pink. Therefore, to ensure a better SPD fusion effect, it is more appropriate to require the first visible light source and the second visible light source to have similar chromaticity coordinates.

Figure 3:
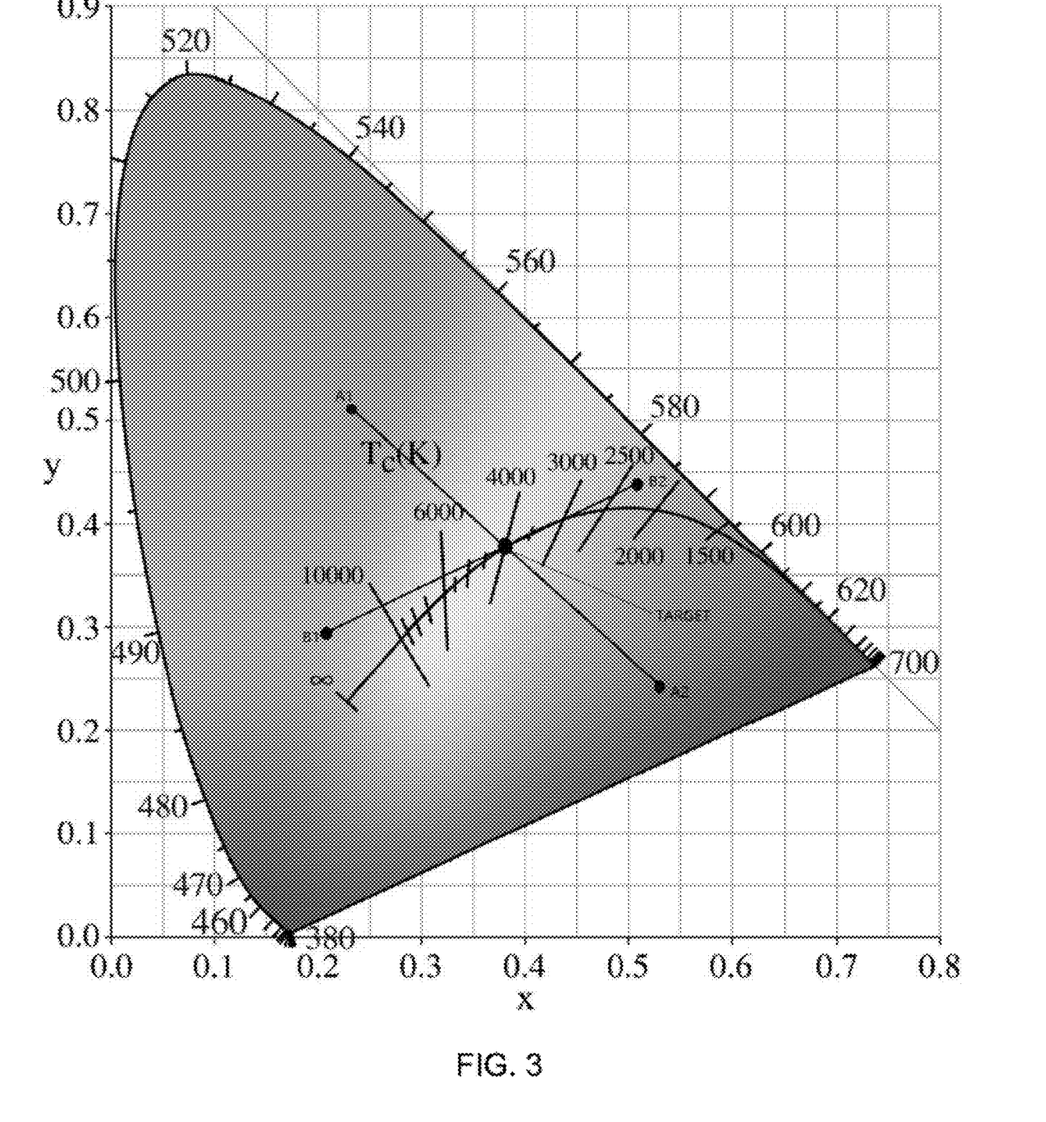
FIG. 3 schematically depicts the forming a target chromaticity coordinate using different combinations of other chromaticity coordinates.

In some embodiments, the first visible light source comprises one or more types of light emitting diode (LED) and the second visible light source comprises one or more types of LED. LED is a preferred light source medium for the first visible light source and the second visible light source, because LED light source can also be turned on/off any high frequency. LED can also be made with a specific or a narrow-band SPD. Moreover, it is feasible to use multiple LED's each with a different SPD to form a blended SPD. In FIG. 3, a TARGET chromaticity coordinate is denoted on the CIE 1931 color space chromaticity diagram. The blending (i.e., a linear combination) of two chromaticity coordinates, A1 (corresponding to an LED source A1) and A2 (corresponding to an LED source A2), can result in a blended color at the TARGET chromaticity coordinate. Similarly, the blending (i.e., a linear combination) of two other chromaticity coordinates, B1 (corresponding to an LED source B1) and B2 (corresponding to an LED source B2), can result in the same blended color at the TARGET chromaticity coordinate. It is evident that the blended SPD with the LED source A1 (green) and the LED source A2 (red) would be very different from the blended SPD with the LED source B1 (cyan) and the LED source B2 (orange). Note that the linear combination of two chromaticity coordinates, A1 and A2 (i.e., the linear combination of SPDs of the LED source A1 and the LED source A2) may not be of equal weight, so long it can result in the TARGET chromaticity coordinate. The same can be said about the linear combination of two chromaticity coordinates, B1 and B2. Moreover, there is no restriction on how many distinct SPD's (i.e., how many chromaticity coordinates) may be used for arriving a target chromaticity coordinate. Thus, it is foreseeable to use two LED light sources (one more yellow and the other darker orange) to produce a chromaticity coordinate similar to the LED source B2 (orange).

It is foreseeable to implement the chromaticity coordinates A1, A2, B1, and B2 using narrow band LED's. In this case, the SPD of the linear combination of the lights of B1 and B2 LED light sources will have very little wavelength overlap to the SPD of the linear combination of the lights of A1 and A2 LED light sources. As a result, the SPD of the linear combination of the lights of B1 and B2 LED light sources and the SPD of the linear combination of the lights of A1 and A2 light sources differ more than 5% in almost all 50 nm wavelength ranges from 400 nm to 750 nm, e.g., in [400 nm, 450 nm], [465 nm, 515 nm], [500 nm, 550 nm], etc.

As just mentioned, it is feasible to construct two visible light sources that their SPD differs more than 5% in one or more 50 nm wavelength ranges in [380 nm, 750 nm] by using narrow-band LED's). However, ipRGCs do not have the same sensitivity across all wavelengths or wavelength ranges. ipRGCs are most sensitive to the wavelength range [465 nm, 515 nm]. It is thus beneficial to select the first and the second visible light sources such that their key SPD difference lies in the wavelength range [465 nm, 515 nm]. In some embodiments, the percentage of the first SPD differs more than 5% over the percentage of the second SPD in the wavelength range [465 nm, 515 nm]. It is foreseeable that in practice, the SPD difference is over 10% in the wavelength range [465 nm, 515 nm] in order to produce a stronger stimulation of the ipRGCs when toggling the first visible light source and the second visible light source. Note that the more than 5% SPD difference in the wavelength range [465 nm, 515 nm] is preferred, but not required. If an embodiment of the present disclosure has more than 5% SPD difference not in the wavelength range [465 nm, 515 nm] but rather outside of the wavelength range [465 nm, 515 nm], it would still work. It is just that it would take a longer exposure time when using this embodiment on an Alzheimer's patient to produce the same amount of stimulation to ipRGCs as compared to using an embodiment of the present disclosure having more than 5% SPD difference in the wavelength range [465 nm, 515 nm].

In addition to using the SPD percentage difference over a 50 nm wavelength range to set the difference between the first visible light source and the second visible light source, another metric, namely, the melanopic ratio (MR) difference, may be used. This is because it is feasible to have two light sources emitting two lights with similar chromaticity coordinates on the CIE 1931 color space chromaticity diagram but with different MR's. A light with a higher MR will generate stronger stimulus to the ipRGCs as compared to a light with a lower MR. Thus, when toggling two light sources with similar chromaticity coordinates but a wider difference on their MR's, it could lead to a stronger toggling effect to the ipRGCs, yet without causing any visual discomfort since they have similar chromaticity coordinates. In some embodiments, the MR of the first visible light source is greater than the MR of the second visible light source. For example, in FIG. 3, the MR of a first visible light source comprising the LED source B1 (cyan) and the LED source B2 (orange) is greater than the MR of a second visible light source comprising the LED source A1 (green) and the LED source A2 (red). Further in some embodiments, the MR of the first visible light source (e.g., 0.86) is greater than the MR of the second visible light source (e.g., 0.60) by 0.2. The 0.2 difference in the MR values between first visible light source and the second visible light source ensures there is sufficient non-visual toggling effect for stimulating the ipRGCs.

In the embodiments, the toggling frequency of the first visible light source and the second visible light source falls between 35 to 45 Hz. The has been shown that the toggling frequency at 40 Hz can induced the best simulation for certain brain cells.

The apparatus has only one driver circuit for driving the first visible light source and the second visible light source alternately. There are different embodiments of the driver circuit for alternating its fixed internal power to power either the first visible light source or the second visible light source. In some embodiments, the driver circuit has one output power port through which the fixed internal power flows through. The controller is configured to connect, according to its toggling operation, either the first visible light source or the second visible light source to this one output power port for receiving the fixed internal power. In some other embodiments, the driver circuit has a first output power port connecting to the first visible light source and a second output power port connecting to the second visible light source. The controller is configured to activate, according to its toggling operation, either the first output power port or the second output power port for receiving the fixed internal power.

In some embodiments, the apparatus further comprises a sound wave generator. In conjunction with the toggling operation of the first visible light source and the second visible light source, the controller is configured to trigger the sound wave generator to generate a sound wave at a frequency the same as the toggling frequency of the first visible light source and the second visible light source. Having both visual and audible stimulations could potentially double the effect of stimulating certain brain cells, resulting a more effective treatment to Alzheimer's disease. The controller may toggle the first visible light source and the second visible light source and trigger the sound wave generate simultaneously. However, it is not required for the controller to toggle the light sources and trigger the sound wave generator for the same amount of time. For example, the controller may trigger the sound wave generate to generate a sound wave for only 2 minutes, whereas the controller may toggle the light sources for 10 minutes.

Further in some embodiments, the sound wave generator generates a sinusoidal sound wave, as opposed to a square sound wave. A square sound wave is harsher and more uncomfortable to ears as compared to a sinusoidal sound wave. Thus, using a sinusoidal sound wave may lead to a better user adoption or a longer treatment time, resulting a more effective treatment of Alzheimer's disease.

In another aspect, the SPD fusion method comprises toggling the turning on of a first visible light source and a second visible light source at a toggling frequency>25 Hz. The first visible light source is turned on during one half of the duty cycle (though not necessarily to be on for the entire half cycle), whereas the second visible light source is turned on during the other half of the duty cycle (though not necessarily to be on for the entire other half cycle). The first visible light source and the second visible light emit similar light outputs. Moreover, the first visible light source and the second visible light emit similar light outputs. The first visible light source has a first SPD and the second visible light source with a second SPD. The first SPD is different from the second SPD in that in a 50 nm wavelength range within [380 nm, 750 nm] the percentage of the first SPD in this 50 nm wavelength range differs more than 5% over the percentage of the second SPD in this 50 nm wavelength range. Lastly, the chromaticity (x, y) coordinate of the light emitted by the first visible light on the CIE 1931 color space chromaticity diagram is adjacent to the chromaticity (x, y) coordinate of the light emitted by the second visible light on the CIE 1931 color space chromaticity diagram. The chromaticity coordinate of the light emitted by the first visible light on the CIE 1931 color space chromaticity diagram is not required to be the same as the chromaticity coordinate of the light emitted by the second visible light, so long as they are close enough to each other to the extend they are not distinguishable by human eyes.

In some embodiments, the first visible light source comprises one or more types of light emitting diode (LED) and the second visible light source comprises one or more types of LED. LED is a preferred light source medium for the first visible light source and the second visible light source, because LED light source can also be turned on/off any high frequency. LED can also be made with a specific or a narrow-band SPD. Moreover, it is feasible to use multiple LED's each with a different SPD to form a blended SPD.

In some embodiments, the percentage of the first SPD differs more than 5% over the percentage of the second SPD in the wavelength range [465 nm, 515 nm]. It is foreseeable that in practice, the SPD difference is over 10% in the wavelength range [465 nm, 515 nm] in order to produce a stronger stimulation of the ipRGCs when toggling the first visible light source and the second visible light source.

In some embodiments, the MR of the first visible light source is greater than the MR of the second visible light source. Further in some embodiments, the MR of the first visible light source is greater than the MR of the second visible light source by 0.2, thus the SPD of the first visible light source and the SPD of the second visible light source is markedly different according to the MR metric.

In some embodiments, the toggling frequency of the first visible light source and the second visible light source falls between 35 to 45 Hz frequency range. Within this frequency range, the frequency 40 Hz is preferred.

In some embodiments, in conjunction with the toggling of the first visible light source and the second light visible light source, the method further comprises generating a sound wave, at a frequency the same as the toggling frequency of the first visible light source and the second visible light source. Further in some embodiments, the sound wave is a sinusoidal sound wave, as opposed to a square sound wave.

BRIEF DESCRIPTION OF THE DRAWINGS

The accompanying drawings are included to aid further understanding of the present disclosure and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting apparatuses having different form factors.

The present disclosure discloses an SPD fusion lighting apparatus includes a first visible light source with a first SPD, a second visible light source with a second SPD, a driver circuit, and a controller. The first SPD is different than the second SPD markedly in a 50 nm wavelength range. The controller toggles the turning on of the first visible light and the second visible light at a frequency>25 Hz. The first visible light source is turned on during one half of the duty cycle, whereas the second visible light source is turned on during the other half of the duty cycle. The first visible light source and the second visible light emit similar light outputs and have similar chromaticity coordinates on the CIE 1931 color space chromaticity diagram.

Example Implementations

Figure 4:
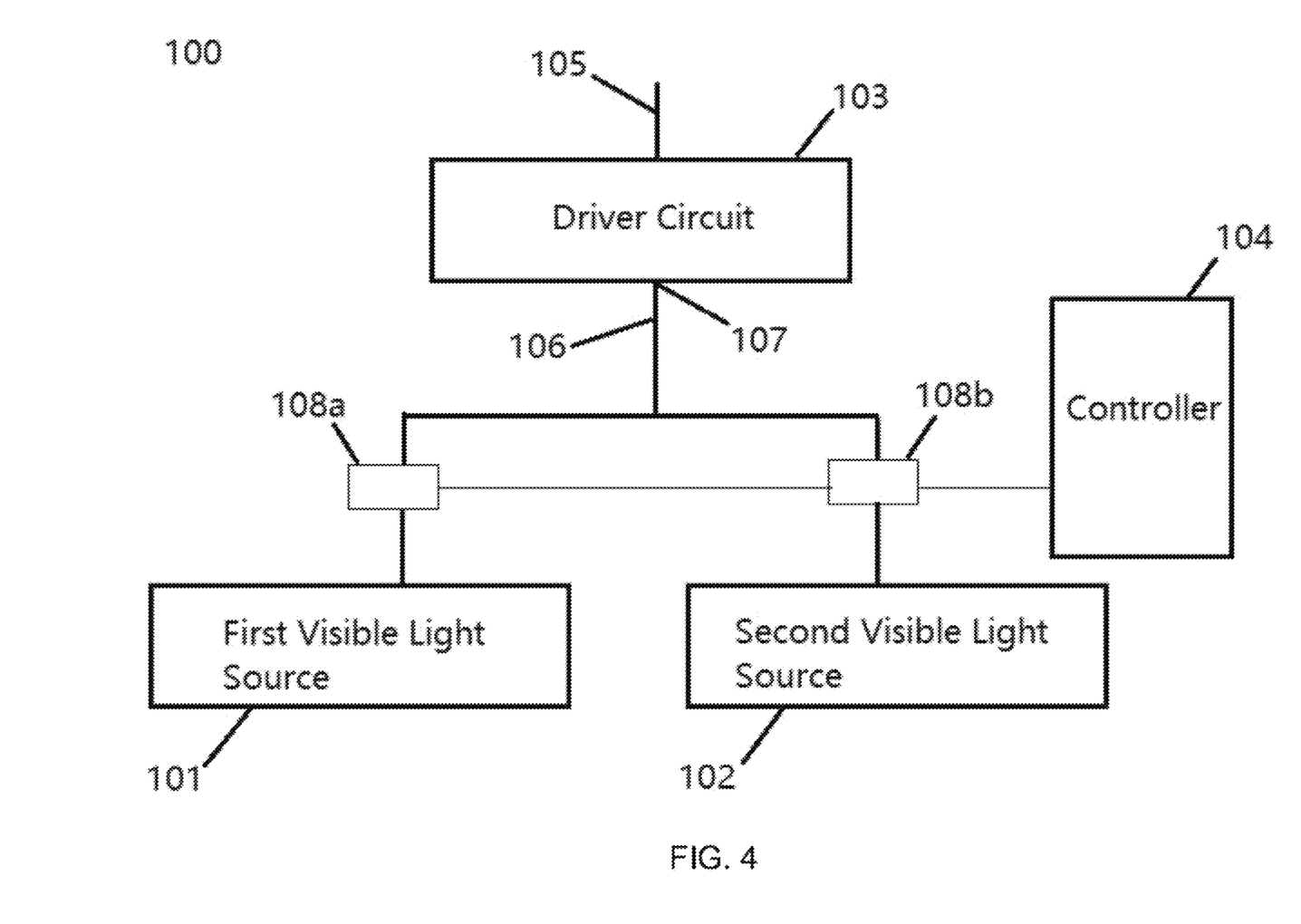
FIG. 4 schematically depicts an embodiment of the present disclosure with the driver circuit having one output power port.

FIG. 4 is an embodiment of the SPD fusion lighting apparatus of the present disclosure. The embodiment 100 has a first visible light source 101, a second visible light source 102, a driver circuit 103, and a controller 104. The first visible light source is a 4000K full spectrum LED with its SPD shown in FIG. 1, whereas the second visible light source is a typical 4000K LED with its SPD also shown in FIG. 1. Their SPD differs more than 5% in the [465 nm, 515 nm] wavelength range. The two visible light sources have the same chromaticity coordinate TARGET on the CIE 1931 color space chromaticity diagram as shown in FIG. 3. The controller 104 is configured to toggle the turning on of the first visible light source 101 and the second visible light source 102 at a toggling frequency 40 Hz. The controller 104 turns on the first visible light source 101 during the first half of the duty cycle and the second visible light source 102 during the second half of the duty cycle. When the first visible light source 101 and the second visible light source 102 are turned on, they are on for the entire half duty cycle (though this is not required). The first visible light source 101 and the second visible light source 102 emit similar light outputs. Thus, human eyes cannot distinguish the light emitted by the first visible light source 101 from the light emitted by the second visible light source 102. The driver circuit 103 converts an external power 105 to a fixed internal power 106 to power either the first visible light source 101 or the second visible light source 102. The driver circuit 103 has one output power port 107 through which the fixed internal power 106 flows through. The controller 104 is configured to connect, according to its toggling operation, either the first visible light source 101 (via a switching component 108a) or the second visible light source 102 (via another switching component 108b) to the output power port 107 for receiving the fixed internal power 106.

Figure 5:
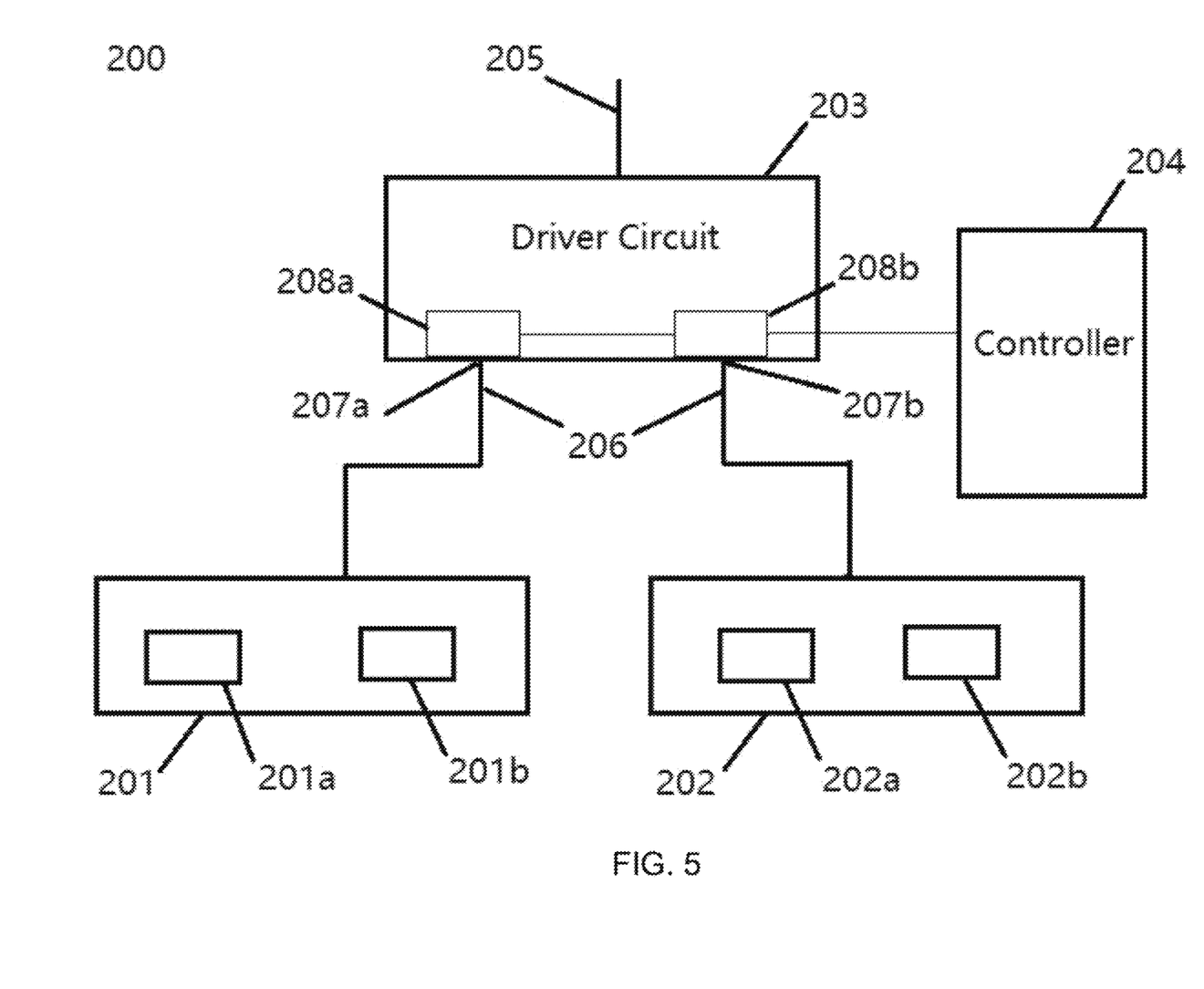
FIG. 5 schematically depicts an embodiment of the present disclosure with the driver circuit having two output power ports.

FIG. 5 is another embodiment of the SPD fusion lighting apparatus of the present disclosure. The embodiment 200 has a first visible light source 201, a second visible light source 202, a driver circuit 203, and a controller 204. The first visible light source 201 comprises two types of narrow band LED's, 201a and 201b, and the second visible light source 202 comprises two types of narrow band LED's, 202a and 202b. LED 201a emits a light having a chromaticity coordinate B1 as shown in FIG. 3, and LED 201b emits a light having a chromaticity coordinate B2. The combination of the lights emitted by LED 201a and LED 201b has a chromaticity coordinate TARGET as shown in FIG. 3. Similarly, LED 202a emits a light having a chromaticity coordinate A1 as shown in FIG. 3, and LED 202b emits a light having a chromaticity coordinate A2. The combination of the lights emitted by LED 202a and LED 202b has the same chromaticity coordinate TARGET as shown in FIG. 3. Though not shown, the SPD of the first visible light source 201 in the [465 nm, 515 nm] wavelength range is 14%, and the SPD of the second visible light source 202 in the same wavelength range is 4%. This can be seen from the fact that the narrow band LED 201a having B1 chromaticity coordinate is rich in cyan wavelength (475 nm-495 nm), while narrow band LED 202a and 202b have very low SPDs in the wavelength range [465 nm, 515 nm]. For the same reason, the combination of the lights emitted by narrow band LED 201a and LED 201b has a higher MR ratio 0.86, whereas the combination of the lights emitted by narrow band LED 202a and LED 202b has a lower MR ration 0.60.

The controller 204 is configured to toggle the turning on of the first visible light source 201 and the second visible light source 202 at a toggling frequency 40 Hz. The controller 204 turns on the first visible light source 201 during the first half of the duty cycle and the second visible light source 202 during the second half of the duty cycle. When the first visible light source 201 and the second visible light source 202 are turned on, they are on for the entire half duty cycle (though this is not required). The first visible light source 201 and the second visible light source 202 emit similar light outputs. Thus, human eyes cannot distinguish the light emitted by the first visible light source 201 from the light emitted by the second visible light source 202. The driver circuit 203 converts an external power 205 to a fixed internal power 206, which will be supplied to either the first visible light source 201 through the first output power port 207a or the second visible light source 202 through the second output power port 207b. The controller 204 is configured to activate, according to its toggling operation, either the first output port 207a (via a switching component 208a) thus enabling the first visible light source 201 for receiving the fixed internal power 206, or the second output port 207b (via a switching component 208b) thus enabling the second visible light source 202 for receiving the fixed internal power 206.

Figure 6:
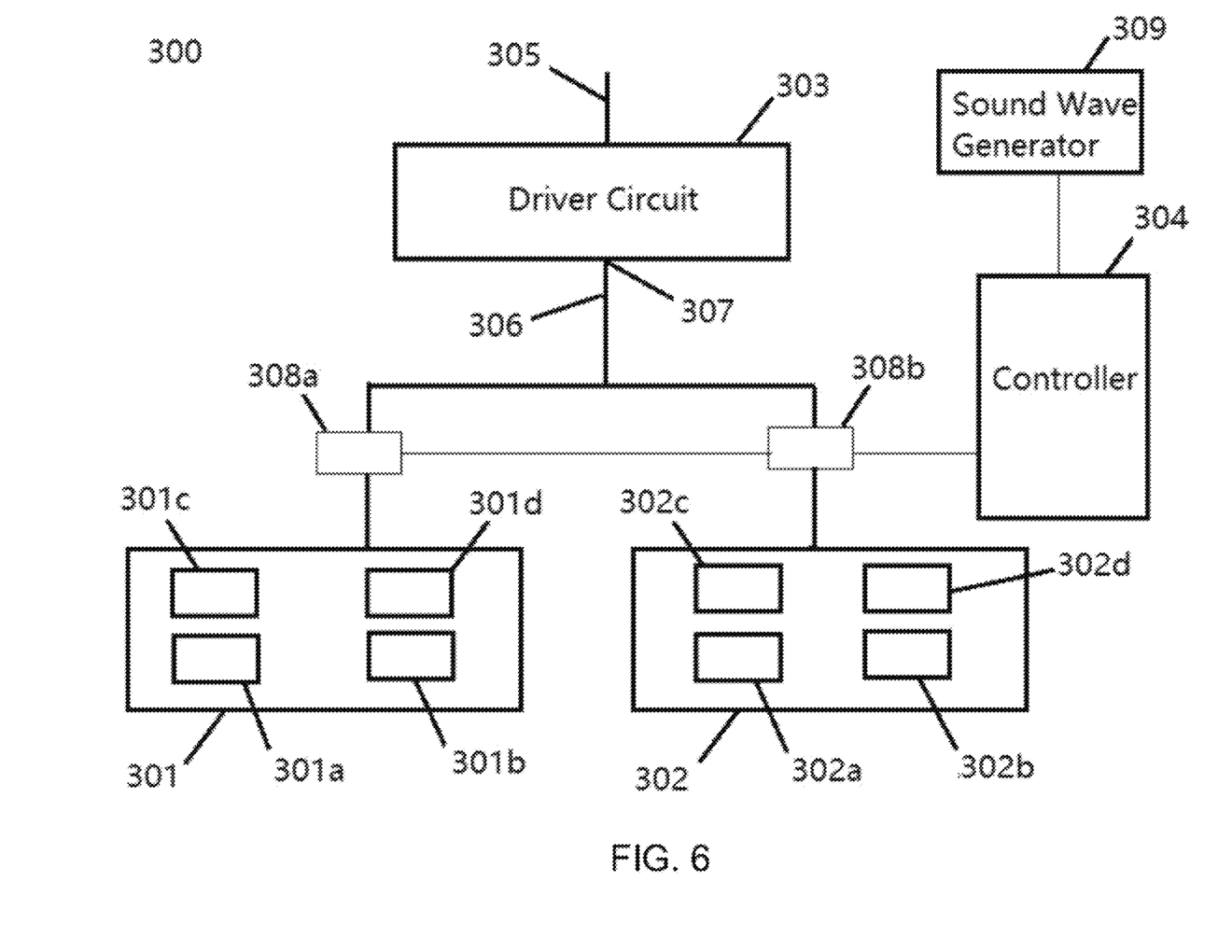
FIG. 6 schematically depicts an embodiment of the present disclosure with a sound wave generator.

FIG. 6 is another embodiment of the SPD fusion lighting apparatus of the present disclosure. The embodiment 300 has a first visible light source 301, a second visible light source 302, a driver circuit 303, a controller 304, and a sound wave generator 309. The first visible light source 301 comprises four types of narrow band LED, 301a, 301b, 301c, and 301d, corresponding to the chromaticity coordinates B1, B2, A1, and A2 (as shown in FIG. 3), respectively. Their combined light output has the chromaticity coordinate TARGET. The second visible light source uses only one type of LED. The LED's 302a, 302b, 302c, and 302d are of the same type, a typical 4000K LED having the chromaticity coordinate TARGET with its SPD shown in FIG. 1. Though not shown, the SPD of the first visible light source 301 in the [465 nm, 515 nm] wavelength range differs more than 5% than the SPD of the second visible light source 302 in the same wavelength range. This is attributed to the narrow band LED 301a (corresponding to the chromaticity coordinates B1) whose SPD is high in cyan wavelength (475 nm-495 nm) while the SPD of the second visible light source 302 is very low in the same wavelength range.

The controller 304 is configured to toggle the turning on of the first visible light source 301 and the second visible light source 302 at a toggling frequency 40 Hz. The controller 304 turns on the first visible light source 301 during the first half of the duty cycle and the second visible light source 302 during the second half of the duty cycle. When the first visible light source 301 and the second visible light source 302 are turned on, they are on for the entire half duty cycle (though this is not required). The first visible light source 301 and the second visible light source 302 emit similar light outputs. Thus, human eyes cannot distinguish the light emitted by the first visible light source 301 from the light emitted by the second visible light source 302. The driver circuit 303 converts an external power 305 to a fixed internal power 306 to power either the first visible light source 301 or the second visible light source 302. The driver circuit 303 has one output power port 307 through which the fixed internal power 306 flows through. The controller 304 is configured to connect, according to its toggling operation, either the first visible light source 301 (via a switching component 308a) or the second visible light source 302 (via another switching component 308b) to the output power port 307 for receiving the fixed internal power 306. When the controller 304 toggles the turning on of the first visible light source 301 and the second visible light source 302 at 40 Hz, it triggers simultaneously the source generator 309 to generate a sinusoidal sound wave at 40 Hz.

Additional and Alternative Implementation Notes

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A spectral power distribution (SPD) fusion lighting apparatus, comprising
a first visible light source with a first SPD;
a second visible light source with a second SPD;
a driver circuit; and
a controller,
wherein:
the first SPD is different from the second SPD in that, in a 50 nm wavelength range within [380 nm, 750 nm], a percentage of the first SPD in this 50 nm wavelength range differs more than 5% over a percentage of the second SPD in this 50 nm wavelength range;
a chromaticity (x, y) coordinate of a first light emitted by the first visible light source on an International Commission on Illumination in 1931 (CIE 1931) color space chromaticity diagram is adjacent to a chromaticity (x, y) coordinate of a second light emitted by the second visible light source on the CIE 1931 color space chromaticity diagram;
the controller is configured to toggle on and off the first visible light source and the second visible light source at a toggling frequency greater than 25 Hz, such that:
the first visible light source is turned on during one half of a duty cycle,
the second visible light source is turned on during the other half of the duty cycle,
the first visible light source and the second visible light emit similar light outputs; and
the driver circuit is configured to convert an external power to a fixed internal power to power either the first visible light source or the second visible light source according to a toggling operation by the controller between the first visible light source and the second visible light source.

2. The apparatus of claim 1, wherein the first visible light source comprises one or more types of light emitting diode (LED), and wherein the second visible light source comprises one or more types of LED.

3. The apparatus of claim 1, wherein the percentage of the first SPD differs more than 5% over the percentage of the second SPD in a wavelength range of [465 nm, 515 nm].

4. The apparatus of claim 1, wherein a melanopic ratio (MR) of the first visible light source is greater than the MR of the second visible light source by 0.2.

5. The apparatus of claim 1, wherein the toggling frequency of the first visible light source and the second visible light source falls between 35 to 45 Hz.

6. The apparatus of claim 1, wherein the driver circuit has one output power port through which the fixed internal power flows, and wherein the controller is configured to connect, according to its toggling operation, either the first visible light source or the second visible light source to this one output power port to receive the fixed internal power.

7. The apparatus of claim 1, wherein the driver circuit has a first output power port connecting to the first visible light source and a second output power port connecting to the second visible light source, and wherein the controller is configured to activate, according to its toggling operation, either the first output power port or the second output power port to receive the fixed internal power.

8. The apparatus of claim 1, further comprising:
a sound wave generator, wherein in conjunction with the toggling operation of the first visible light source and the second visible light source, the controller is configured to trigger the sound wave generator to generate a sound wave at a frequency that is same as the toggling frequency of the first visible light source and the second visible light source.

9. The apparatus of claim 8, wherein the sound wave generator is configured to generate a sinusoidal sound wave.

10. A spectral power distribution (SPD) fusion method, comprising
toggling on and off a first visible light source and a second visible light source at a toggling frequency greater than 25 Hz, such that:

the first visible light source is turned on during one half of a duty cycle, the second visible light source is turned on during the other half of the duty cycle, the first visible light source and the second visible light emit similar light outputs, wherein, the first visible light source is configured with a first SPD, the second visible light source is configured with a second SPD, the first SPD is different from the second SPD in that, in a 50 nm wavelength range within [380 nm, 750 nm], a percentage of the first SPD in this 50 nm wavelength range differs more than 5% over a percentage of the second SPD in this 50 nm wavelength range, and a chromaticity (x, y) coordinate of a first light emitted by the first visible light source on an International Commission on Illumination in 1931 (CIE 1931) color space chromaticity diagram is adjacent to a chromaticity (x, y) coordinate of a second light emitted by the second visible light source on the CIE 1931 color space chromaticity diagram.

11. The method of claim 10, wherein the first visible light source comprises one or more types of light emitting diode (LED), and wherein the second visible light source comprises one or more types of LED.

12. The method of claim 10, wherein the percentage of the first SPD differs more than 5% over the percentage of the second SPD in a wavelength range of [465 nm, 515 nm].

13. The method of claim 10, wherein a melanopic ratio (MR) of the first visible light source is greater than the MR of the second visible light source by 0.2.

14. The method of claim 10, wherein the toggling frequency of the first visible light source and the second visible light source falls between 35 to 45 Hz.

15. The method of claim 10, in conjunction with the toggling of the first visible light source and the second light visible light source, further comprising:

generating a sound wave, at a frequency that is same as the toggling frequency of the first visible light source and the second visible light source.

16. The method of claim 15, wherein the sound wave is a sinusoidal sound wave.

* * * * *